United States Patent

Horwell et al.

[11] 4,215,074
[45] Jul. 29, 1980

[54] PROCESS FOR PREPARING CIS-BICYCLOOCTYLAMINES

[75] Inventors: David C. Horwell, Farnborough; Graham H. Timms, Camberley, both of England

[73] Assignee: Lilly Industries Limited, London, England

[21] Appl. No.: 49,672

[22] Filed: Jun. 18, 1979

[30] Foreign Application Priority Data

Jul. 15, 1978 [GB] United Kingdom ............... 29988/78

[51] Int. Cl.² ............................................. C07C 83/00
[52] U.S. Cl. ................................. 260/563 P; 424/325; 424/330; 260/570.5 R
[58] Field of Search ......................... 260/563 P, 570.5

[56] References Cited

U.S. PATENT DOCUMENTS

| | | |
|---|---|---|
| 3,228,984 | 1/1966 | Humber ............................ 260/563 P |
| 3,264,351 | 8/1966 | Humber ........................ 260/563 P X |
| 3,515,740 | 6/1970 | Frampton .................... 260/563 P X |

Primary Examiner—Paul F. Shaver
Attorney, Agent, or Firm—James L. Rowe; Arthur R. Whale

[57] ABSTRACT

A process for preparing antidepresssant 2-phenylbicyclooctylamines of formula (I):

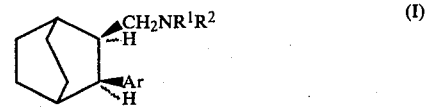

where $R^1$ and $R^2$ represent $C_{1-3}$ alkyl and Ar represents a phenyl group optionally substituted by up to two halogen atoms, by reduction of a novel enamine intermediate of formula:

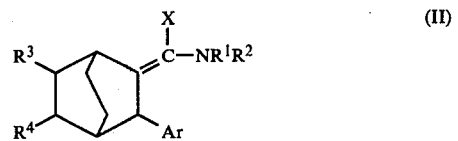

where $R^3$ and $R^4$ are hydrogen or taken together represent a single bond and where X is hydrogen, bromine or chlorine.

5 Claims, No Drawings

PROCESS FOR PREPARING CIS-BICYCLOOCTYLAMINES

This invention relates to a novel process for preparing 2-phenylbicyclooctanes and to a novel class of intermediates of value in this process.

In West German Offenlegungsschrift No. 2,619,617 a class of cis-bicyclooctylamine derivatives are described which possess antidepressant activity and which are therefore useful in the treatment of various depressive states in mammals. It has been found that compounds of formula (I):

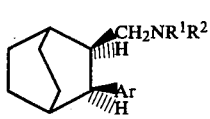
(I)

where $R^1$ and $R^2$ represent $C_{1-3}$ alkyl and Ar represents a phenyl group optionally substituted by up to two halogen atoms, and their pharmaceutically-acceptable salts, are particularly promising antidepressant agents.

The synthetic methods described in the above Offenlegungsschrift for the preparation of compounds of formula (I) involve a multi-stage process which is rather cumbersome. The present process enables the production of compounds of formula (I) from readily available starting materials in a simple and elegant manner.

According to the present invention there is provided a process for preparing a compound of formula (I) which comprises reducing a compound of formula (II):

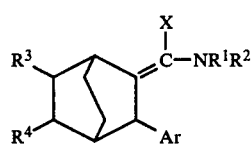
(II)

wherein $R^1$, $R^2$ and Ar are as previously defined, X is hydrogen bromine or chlorine and either $R^3$ and $R^4$ are hydrogen or taken together represent a single bond.

The reduction can be accomplished catalytically using hydrogen over a group (VIII) metal such as platinum or palladium. Reaction temperatures of from $-20°$ C. to $100°$ C., for example from $0°$ C. to $100°$ C., can be used to effect the reaction which is normally complete within 24 hours. Of course, when $R^3$ and $R^4$ taken together represent a chemical bond, an extra mole of hydrogen is required to complete the reduction.

The preferred catalyst is $PtO_2$ (Adams catalyst) which when used in conjunction with a polar organic solvent such as an alkanol, for example methanol, ethanol and isopropanol, or ethyl acetate, allows the production of pure cis compounds of formula (I), contaminated with only small amounts of the corresponding trans-isomer, for example less than 15 percent and more preferably less than 5 percent.

The process of the invention is preferred when $R^1$ and $R^2$ are methyl and Ar is 3,4-dichlorophenyl since this process leads to a particularly active compound of formula (I).

Compounds of formula (II) are novel and are provided in a further aspect of the invention. Their preparation from readily available starting materials can be illustrated by the following reaction scheme:

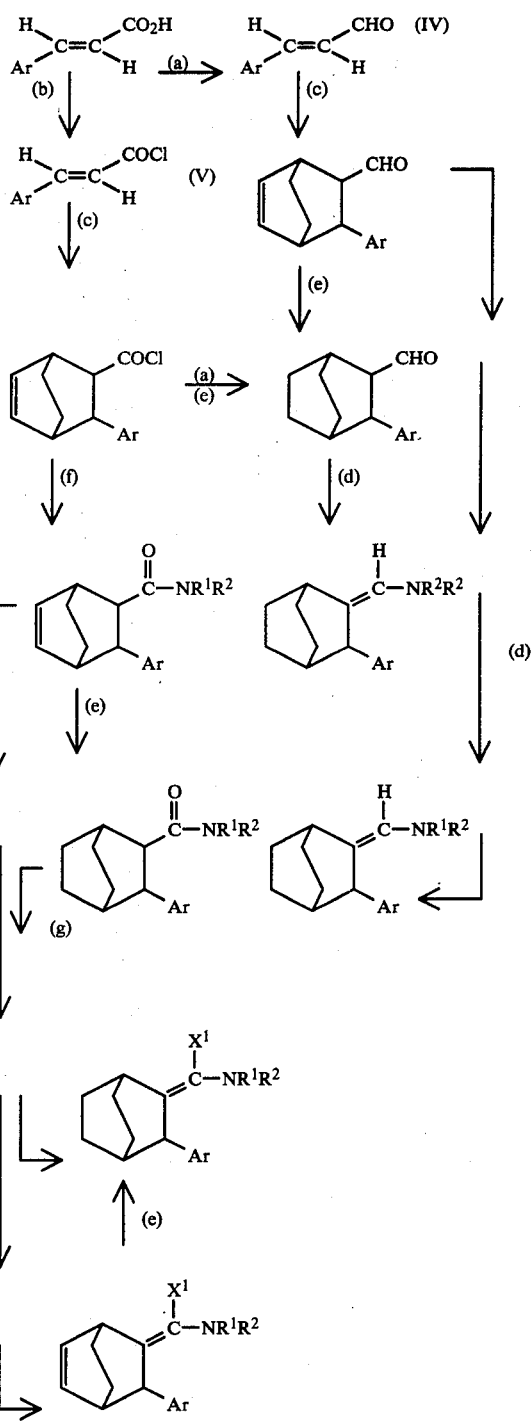

where $X^1$ is bromine or chlorine.

Reaction (a) is a reduction which can be carried out via the corresponding acid chloride using conventional Rosenmund reduction conditions and reagents.

The chlorination reaction (b) may be effected using conventional chlorinating agents such as thionyl chloride or oxalyl chloride.

Reaction (c) involves a Diels-Alder reaction with 1,3-cyclohexadiene at a temperature between $100°$ and $150°$ C. The acid chloride of formula (V) reacts more quickly with the cyclohexadiene than the aldehyde of formula (IV).

To effect the formation of the enamine by reaction (d) it is necessary to react the aldehyde with the corresponding dialkylamine in the presence of a suitable dehydrating agent such as titanium tetrachloride, molecular sieves (3A) or anhydrous potassium carbonate.

Reaction (e) is a catalytic hydrogenation which can be effected using hydrogen and a palladium on charcoal catalyst in an inert solvent such as ethyl acetate.

Reaction (f) involves the condensation of the acid chloride with excess of the secondary alkylamine of formula $HNR^1R^2$.

Reaction (g) comprises the bromination or chlorination of the amide formed by reaction (f) with a suitable halogenating agent for example phosphorus pentabromide or pentachloride or sulphuryl chloride.

The invention will now be further illustrated with reference to the following non-limitative examples.

EXAMPLE 1

2-(3,4-Dichlorophenyl)-bicyclo[2,2,2]octan-3-N,N-dimethylaminoylidene (a) To trans-2-(3,4-dichlorophenyl)-3-formylbicyclo[2,2,2]octane (2 g, 7.1 mmole) and dimethylamine (5 ml) in benzene (35 ml), was added dropwise titanium tetrachloride (0.67 g, 3.5 mmole) in benzene (15 ml), the temperature being maintained between 0° and 10° C.

The reaction mixture was left at room temperature overnight, filtered and excess solvent evaporated off to give the title product as a white oily solid (yield 2.5 g). The structure of the product was confirmed by its NMR, IR and mass spectra. Distillation of the product could be effected at 180° C./0.03 mm.

(b) A mixture of trans-2-(3,4-dichlorophenyl)-3-formylbicyclo[2,2,2]octane (1 g), molecular sieve type 3A (2 g powder), dimethylamine (1 ml) and benzene (10 ml) was stirred at room temperature for 16 hours. The reaction mixture was filtered and solvent evaporated off to give the title product as a white solid (yield 1.2 g) which soon transformed to an oil, b.p. 180° C. at 0.03 mm. Structure confirmation was again carried out by NMR, IR and mass spectra.

EXAMPLE 2 cis-2-(3,4-Dichlorophenyl)-3-N,N-dimethylaminomethyl-bicyclo[2,2,2]octane

Platinum oxide (106.8 mg) was hydrogenated at room temperature in isopropanol (3 ml). The uptake of hydrogen after twenty minutes was 21.8 ml (theoretical 21.15 ml). The enamine product of Example 1 (189 mg) in isopropanol (2 ml) was then added and the mixture hydrogenated for 45 minutes. The uptake of hydrogen was 14.8 ml (theoretical 13.7 ml). The catalyst was filtered off and the filtrate evaporated to an oil (yield 15.3 mg, 81%). This oil was dissolved in 5 N hydrochloric acid and extracted with ether. The ether extract was washed with water, dried over magnesium sulphate and evaporated to give an oil (yield 70.7 mg, 37%) thus removing neutral components produced during the reaction. The acidic aqueous extract was basified with 5 N NaOH and extracted with ether. The ether was washed with water, dried over anhydrous magnesium sulphate and evaporated to give the title product as an oil (yield 72.9 mg, 38.5%).

Structure confirmation was effected by NMR and GLC. These analytical methods showed that the product of the reaction was very pure cis-material (98%) with only small amounts (2%) of trans-material present as an impurity.

EXAMPLE 3

2-(3,4-Dichlorophenyl)bicyclo[2,2,2]oct-2-ene-3-N,N-dimethylaminoylidene trans-2-(3,4-Dichlorophenyl)-3-formylbicyclo[2,2,2]oct-5-ene (0.26 g, 0.9 mmole), molecular sieves (type 3A powder, 0.52), dimethylamine (0.3 ml) and benzene (5 ml) were stirred for 4 days. The sieves were filtered off and the filtrate evaporated to give the title product as a yellow oil (yield 0.27 g). Structure confirmation was effected by NMR and IR spectral data.

EXAMPLE 4 cis-2-(3,4-Dichlorophenyl)-3-N,N-dimethylaminomethylbicyclo[2,2,2]octane

Platinum oxide (108 mg) was hydrogenated at atmospheric pressure in benzene (3 ml) at room temperature over one hour. Benzene (25 ml) was then added and the mixture was refluxed, using a Dean and Stark apparatus. After 2 hours the catalyst was washed three times with ethanol (30 ml) and, after adding ethanol (3 ml), the catalyst was hydrogenated for an hour. The enamine of Example 3 (235 mg) in ethanol (2 ml) was injected into the apparatus and the mixture was hydrogenated. After 3 hours the uptake of hydrogen was 33.1 ml (theoretical 34.1 ml). The catalyst was filtered off and the filtrate evaporated to give an oil. This was dissolved in 5 N HCl and extracted with ether. The ether extract was washed, dried and evaporated to give an oil (101.5 mg) containing non-basic products. The acid aqueous extracts were basified (5 N NaOH) and extracted with ether. The ether extracts were washed, dried and evaporated to give an oil, (90 mg, 38.3%). NMR, GLC and MS studies showed this oil to be a mixture of 86% of the cis and 14% of the trans isomers.

What is claimed is:

1. A process of preparing a compound of formula (I):

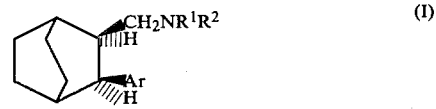

where $R^1$ and $R^2$ and $C_{1-3}$ alkyl, and Ar is a phenyl group optionally substituted by up to two halogen atoms, which comprises reducing a compound of formula (II)

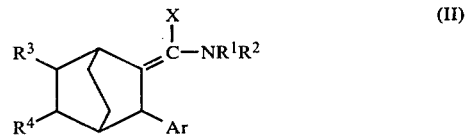

where $R^3$ and $R^4$ are hydrogen or taken together represent a single bond and X is hydrogen, bromine or chlorine.

2. A process according to claim 1 in which the compound of formula (II) is catalytically reduced with hydrogen and $PtO_2$.

3. A process according to either of claims 1 and 2 in which the compound prepared is of formula (I) where $R^1$ and $R^2$ are methyl and Ar is 3,4-dichlorophenyl.

4. A compound of formula (II):
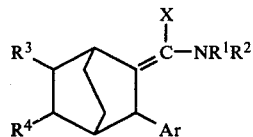
where $R^1$ and $R^2$ are $C_{1-3}$ alkyl, Ar is a phenyl group optionally substituted by up to two halogen atoms, $R^3$ and $R^4$ are hydrogen or taken together represent a single bond, and X is hydrogen, bromine or chlorine.
5. A compound of formula (II) as claimed in claim 4, where X is hydrogen, $R^1$ and $R^2$ are methyl and Ar is 3,4-dichlorophenyl.
* * * * *